April 26, 1955 A. E. LUEDY Plant Pat. 1,388

FASTIGIATE GLOSSY BUCKTHORN PLANT

Filed Feb. 1, 1954

INVENTOR
ARTHUR E. LUEDY
BY Oberlin & Limbach
ATTORNEYS.

United States Patent Office

Plant Pat. 1,388
Patented Apr. 26, 1955

1,388

FASTIGIATE GLOSSY BUCKTHORN PLANT

Arthur E. Luedy, Bedford, Ohio, assignor to The Cole Nursery Company, Painesville, Ohio, a corporation of Ohio Application February 1, 1954, Serial No. 407,622

1 Claim. (Cl. 47—59)

The present invention relates to a new and distinct variety of glossy buckthorn plant originated by me, having a novel and distinctive habit of growth, and more particularly consists in a fastigiate form of glossy buckthorn, *Rhamnus frangula.*

My new buckthorn is a shrub or small tree having a dense, laterally compact habit of growth, very fastigiate, and reaching a height in excess of 12–15 feet when mature. The fruit and leaves are glossy, similar to those of ordinary buckthorns, but the fruits are somewhat more prominently displayed due to its habit of growth.

The leaves are alternate, seldom subopposite, oval or obovate to obovate-oblong, 4 to 9 cm. in length, abruptly acute at the tip, rounded or broad-cuneate at the base, entire with wavy margin, dark glossy green above, somewhat lighter green and sparingly pubescent beneath, with 7 to 9 pair of veins and with the petiole 7 to 20 mm. in length. The flowers are produced in axillary clusters of from 1 to 8. They are glabrous with pedicels 5 to 10 mm. long. The flowers are produced unevenly from early to late June. The fruit is globose 5 to 7 mm. in diameter and develop in color from green to red to dark purple. Often green, red and purple fruit appear in the same cluster at the same time. The fruit ripens in July.

My new buckthorn is characterized by an extraordinarily narrow fastigiate habit of growth and has a medium to rapid rate of growth compared to other buckthorn. The stems and branches are erect and grow close together, often somewhat twining. The one-year twigs are strongly lenticellate and the terminal end is foliate. The stems branch close to the ground so that a substantially uniform density is afforded throughout the height of the plant, a very desirable attribute in a plant commonly employed for hedges. In fact, the habit of growth is so dense and erect that no pruning is necessary for employment of my new buckthorn in hedges although it will ordinarily be desired to prune the top of the same to obtain complete uniformity of height of the specimens comprising the edge. Individual specimens are also useful and decorative as accent points in gardens and in general landscaping.

The original specimen was grown by me from seed selected by me from parent specimens chosen by me for desired characteristics from a great many seedlings which were in turn developed over several generations in a similarly selective manner. I have propagated my new fastigiate glossy buckthorn at Bedford, Ohio, asexually by rooting of cuttings, and it can be very readily propagated in this manner, perpetuating all of its original character.

Referring now more particularly to the annexed drawing.

Figure 1:
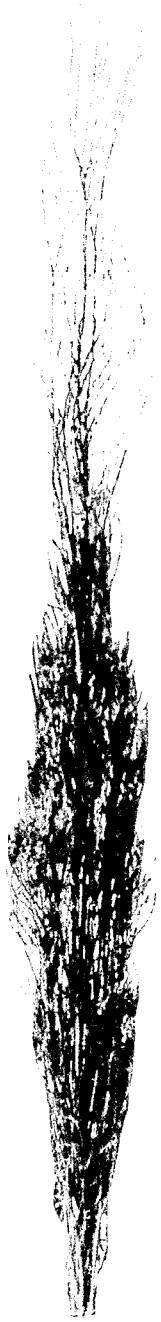
Fig. 1 shows the original specimen at a fairly mature age (approximately 12 feet in height) prior to any pruning and in the winter, without leaves. The dense growth of twigs and branchlets is very obvious as well as the extreme fastigiate habit of growth.
Figure 2:
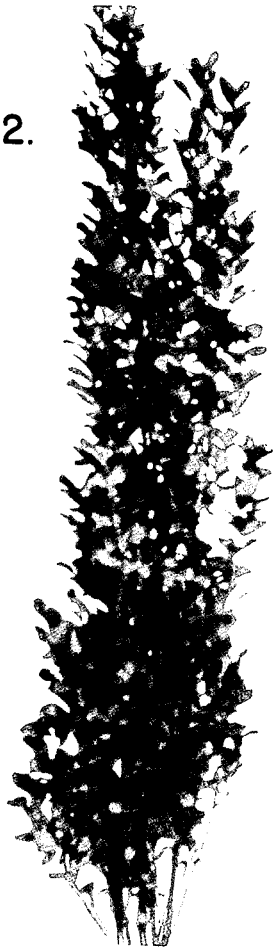
Fig. 2 shows one of the progeny of the Fig. 1 parent (on a relatively enlarged scale) likewise unpruned and in leaf.

The contrast to the normal irregularly spreading habit of growth of the common buckthorn is readily apparent, the common buckthorn requiring to be very frequently pruned or sheared to obtain the desired conformation. In fact, it is ordinarily impossible to force the common buckthorn to assume the extreme fastigiate form illustrated in Fig. 1 even with the most careful pruning.

I claim:

A new and distinct variety of glossy buckthorn plant, *Rhamnus frangula,* having an extremely fastigiate habit of growth, especially as contrasted to the common glossy buckthorn, with the stems and branches erect and laterally compact.

No references cited.